(12) United States Patent
Boyko et al.

(10) Patent No.: US 6,729,190 B1
(45) Date of Patent: May 4, 2004

(54) CERAMIC HONEYCOMB STRENGTH TESTING APPARATUS

(75) Inventors: Ronald A. Boyko, Elmira, NY (US); Cory F. Guenter, Corning, NY (US); James F. King, Jr., Painted Post, NY (US); James E. Lyons, Campbell, NY (US); Chester P. Tuttle, Jr., Corning, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 10/282,638

(22) Filed: Oct. 28, 2002

(51) Int. Cl.[7] .................................................. G01N 3/10
(52) U.S. Cl. ............................. 73/825; 73/818; 73/813
(58) Field of Search ........................... 73/825, 794, 37, 73/818, 826, 806, 816, 813

(56) References Cited

U.S. PATENT DOCUMENTS

| | | | |
|---|---|---|---|
| 4,192,194 A | 3/1980 | Holt | 73/794 |
| 5,339,693 A | 8/1994 | Rowlands et al. | 73/825 |
| 6,405,602 B1 * | 6/2002 | Itou et al. | 73/818 |
| 2002/0157454 A1 | 10/2002 | Shimada et al. | 73/37 |

* cited by examiner

Primary Examiner—Edward Lefkowitz
Assistant Examiner—Alandra Ellington
(74) Attorney, Agent, or Firm—Anca C. Gheorghiu; Scott S. Servilla

(57) ABSTRACT

Methods and apparatus for testing the strength of ceramic honeycomb structures are described. The apparatus includes a chamber that utilizes a flexible, generally cylindrical member including integral flanges to apply compressive force to the periphery of the honeycomb structure. According to some embodiments, a portable apparatus with an open chamber is provided to allow for rapid testing of multiple honeycomb structures.

9 Claims, 4 Drawing Sheets

CERAMIC HONEYCOMB STRENGTH TESTING APPARATUS

FIELD OF THE INVENTION

This invention relates to strength testing of ceramic honeycomb structures. More particularly, the invention relates to apparatus and methods for testing the compressive strength of such structures.

BACKGROUND OF THE INVENTION

Compressive strength is an important feature of thin-walled ceramic honeycomb structures, which are used in the manufacture catalyst supports. Honeycomb structures have a webbed cellular or channeled core structure surrounded in most cases by a smooth integral outer skin layer. The manufacture of structures by extrusion to form cellular ceramic honeycombs of cordierite composition and very low thermal expansion from plasticized mixtures of ceramic batch materials is described in U.S. Pat. Nos. 3,790,654 and 3,885,977. Such honeycombs remain in widespread commercial use as catalyst supports for emissions control applications such as automotive exhaust treatment systems.

One way of improving the exhaust conversion efficiency of catalyst supports is to produce honeycomb products with thinner webs. Currently, the assignee of the present patent application manufactures catalyst supports having web thicknesses in the range of two mils. Thinner webbed structures result in parts that have reduced compressive strength. In the manufacture of exhaust system components, catalyst supports are typically surrounded with a housing comprised of a metal layer. The process for surrounding the parts with a metal layer is known in the art as "canning". The canning process used to place a metal housing around ceramic catalyst supports exerts compressive stresses on the catalyst support. Manufacturers of catalyst supports must be able to provide products that are able to withstand compressive forces encountered during canning processes.

Various apparatus exist for testing compressive strength of ceramic honeycomb structures. One type of apparatus involves enveloping a sample in a rubber boot, immersing the enveloped sample in hydraulic oil and applying isostatic pressure to the sample from all directions. One drawback of this apparatus is that it does not simulate the true compressive forces encountered by catalyst supports during the canning operation. Furthermore, this type of apparatus is relatively large and stationary. In addition, the envelopment, loading and removal of the sample is time consuming, inconvenient for the operator and unclean because the enveloped sample is loaded directly into the hydraulic oil. Since the apparatus is too large to transport, samples must carried to and from the machine. Various apparatus exist for testing tubular products, however, these apparatus do not permit rapid loading, testing and unloading of the product. New methods of testing ceramic honeycomb structures, particularly in a production environment, are needed.

SUMMARY OF THE INVENTION

The invention relates to apparatus and methods for testing the compressive strength of ceramic honeycomb structures. In certain embodiments, a portable compressive strength testing apparatus is provided. According to other embodiments, samples can be easily and rapidly loaded, tested and unloaded from the apparatus. In some embodiments, the portability of the apparatus and the ease and speed of loading, testing and unloading samples facilitates the testing of large quantities of ceramic honeycomb structures. In other embodiments, a failure detector is provided to determine when a part has experienced failure that cannot be detected by visual inspection.

Advantages of the invention will be apparent from the following detailed description. It is to be understood that both the foregoing general description and the following detailed description are exemplary and are intended to provide further explanation of the invention as claimed.

DETAILED DESCRIPTION

Figure 1:
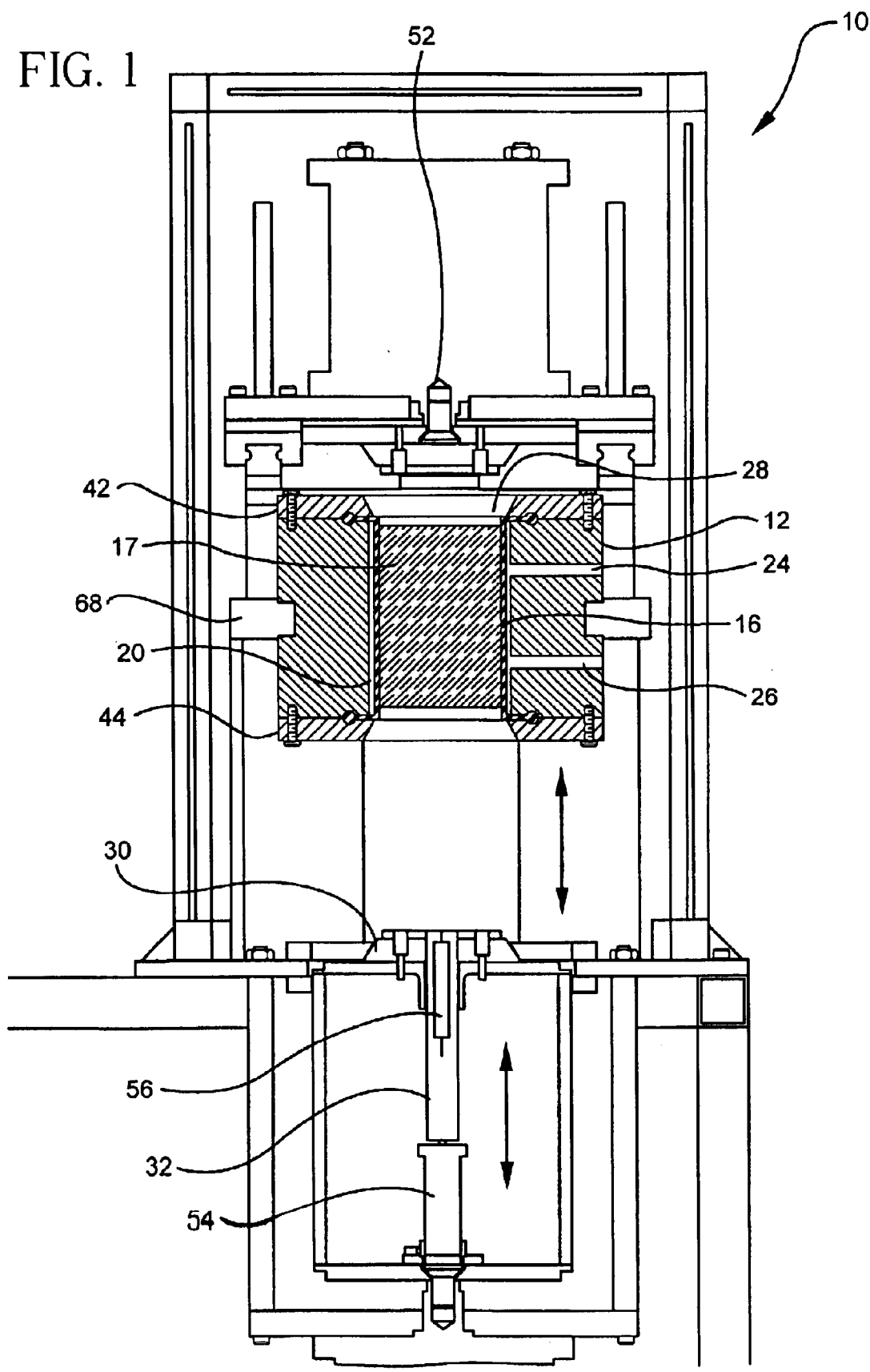
FIG. 1 is a side view of a main housing and loading and unloading portion of the strength testing apparatus according to one embodiment of the invention.

Before describing several exemplary embodiments of the invention, it is to be understood that the invention is not limited to the details of construction or process steps set forth in the following description. The invention is capable of other embodiments and of being practiced or carried out in various ways.

The invention provides apparatus and methods for testing the compressive strength of a ceramic honeycomb samples. Referring to FIGS. 1–4, an exemplary embodiment of an apparatus 10 for testing the compressive strength of ceramic honeycombs is shown. The apparatus 10 includes a main housing 12 having a generally cylindrical chamber 14 and a generally cylindrical, flexible member 16 disposed within the main housing 12. The flexible member 16 defines a sample 17 loading and testing area 18 and a gap 20 between the flexible member and the main housing 12. The gap 20 provides a fluid holding area 22. A fluid inlet 24 and fluid outlet 26 are in fluid communication with a pressure generator 21 for supplying fluid under pressure to the fluid holding area 22 and to expand the flexible member 14 inwardly to provide uniform compressive force on the periphery of the sample 17. A top plug 28 and a bottom plug 30 seal the chamber 14 during testing of the sample 17. The apparatus 10 also includes a mechanism for automatically moving samples 17 in and out the sample loading and testing area. Preferably, the mechanism for moving the sample 17 in and out of the sample loading and testing area includes a retractable plunger 32 that is adapted to move the bottom plug 30 upwardly and downwardly. A top pad 34 is associated with the top plug 28, and a bottom pad 38 is associated with the bottom plug 30. The top pad 34 and bottom pad 38 are in contact with the sample 17 during testing, and should be made from a material that will not chip a ceramic part. The bottom pad 38 also provides lower support for the sample 17 during testing. Preferably, the plunger 32 is hydraulically or pneumatically activated. However, other mechanisms can be used to move sample in and out of the sample loading and testing area. For example, the sample 17 could be moved by a plate supporting the sample 17 attached to a movable screw type mechanism, or the sample could be raised by a support driven by a chain, pulley, belt or other suitable mechanism for raising or lower the sample 17 into the sample test area 18.

Figure 2:
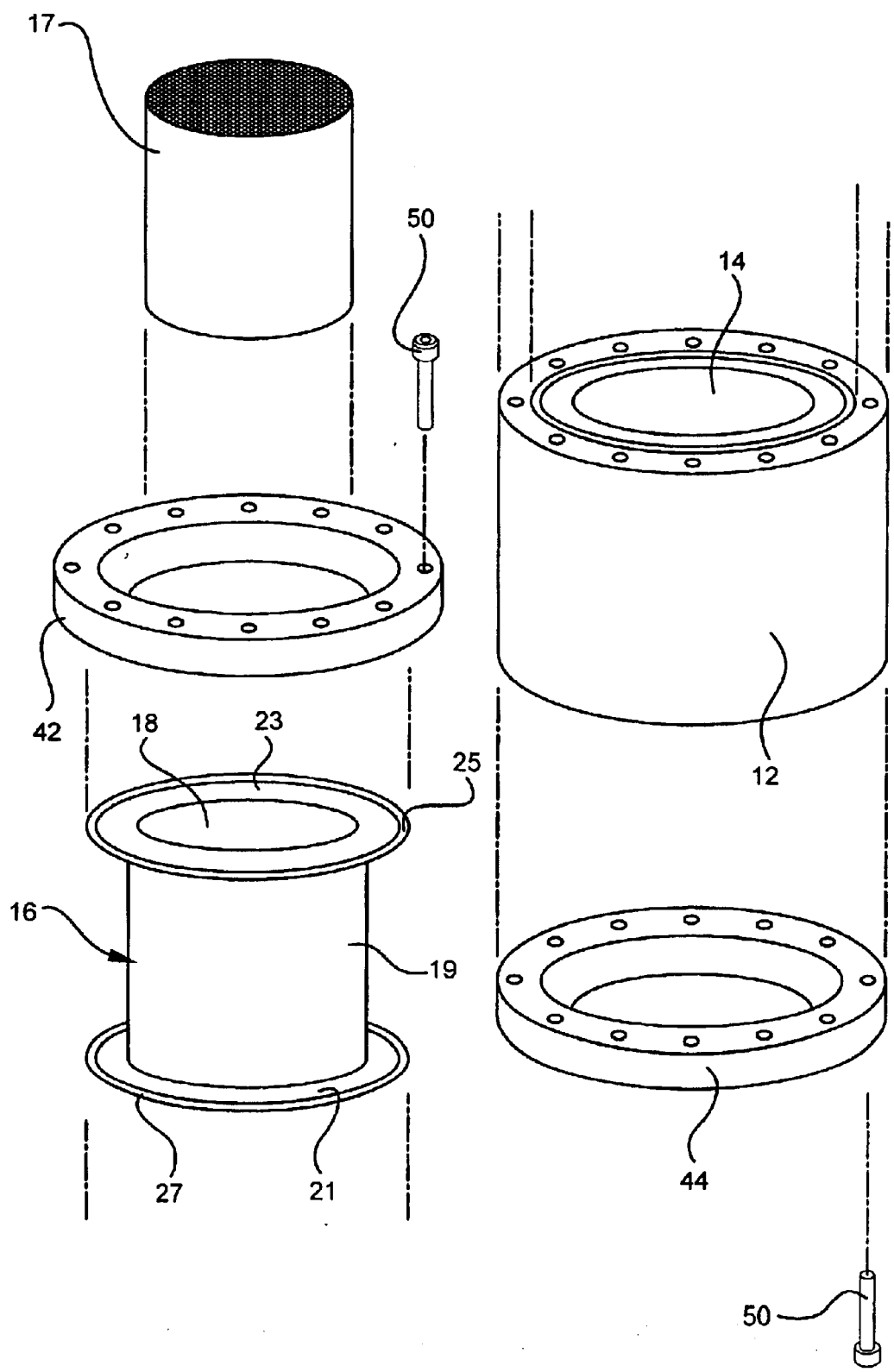
FIG. 2 is an exploded perspective view of a main housing and a flexible member in a honeycomb structure compressive strength testing apparatus according to one embodiment of the invention.

As shown in FIG. 2, the flexible member 16 comprises a generally cylindrical main body 19, a top flange 21 and a bottom flange 23 integrally formed with the main body 19. The flanges 21, 23 extend radially from the top and bottom of the main body. The flanges 21, 23 also include integral gaskets 25, 27 for sealing with the main housing 12. The housing may further include a top recess 40 and a bottom recess (not shown) around the periphery of top and bottom surfaces of the main housing 12. In certain embodiments, the gaskets 25, 27 have a cross-sectional diameter large enough so that the gaskets 25, 27 extend beyond the top and bottom recesses (see FIG. 1). A top sealing cap 42 and a bottom sealing cap 44 are secured to the main housing 12 such that the sealing caps 42 and 44 compress the gaskets 25, 27 to form a fluid tight seal. As shown in the Figures, the sealing caps 42, 44 are secured to the main housing 12 with a plurality of retaining members such as bolts 50. However, the sealing caps 42, 44 can be secured to the main housing 12 by other means such as by clamps.

The main housing 12, the plugs 28, 30 and the sealing rings 42, 44 are preferably made from a metal capable of sustaining the forces generated by the pressure generator and required for compressive strength testing ceramic honeycomb samples. Typically, the chamber is pressurized to pressures between about 50 pounds per square inch and 250 pounds per square inch. The pads 34, 38 are preferably made from a soft material such a polymer or polyurethane. The flexible member 14 is preferably made from polyurethane.

Referring to FIG. 1, preferably the top plug 28, bottom plug 30 and the plunger 42 are retractable such that they can move towards and away from the sample testing area 18 to open and seal the testing area 18. The top plug 28 can be retracted by a pneumatically or hydraulically controlled top plug actuator 52 or other suitable mechanism for moving the plug. The bottom plug 30 can be retracted by pneumatically controlled bottom plug actuator 54 or other suitable mechanism for moving the plug. In preferred embodiments, the bottom pad 38 for supporting the sample 17 can be moved in and out of sample chamber 18 by a pneumatically controlled bottom pad actuator 56.

Figure 4:
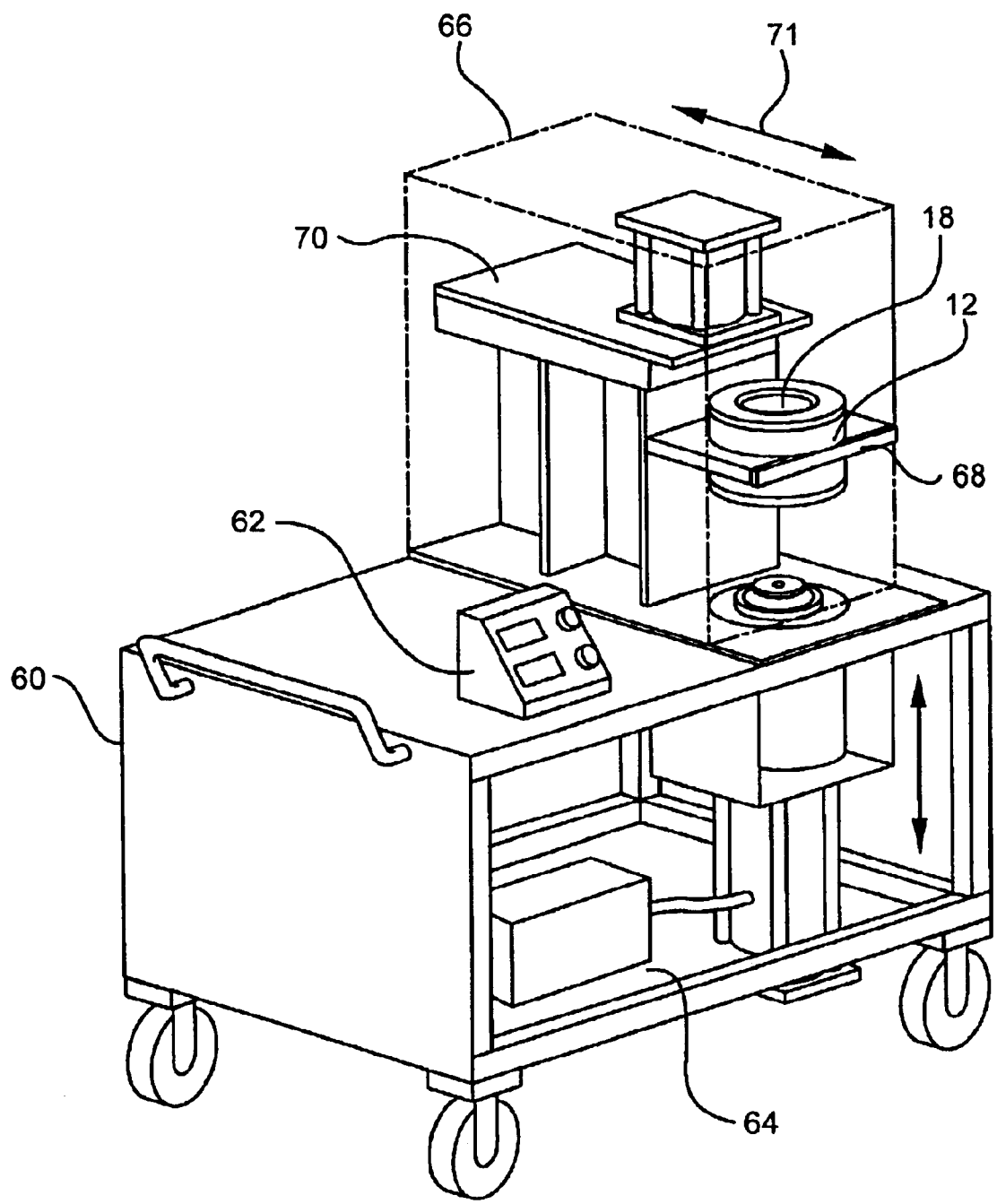
FIG. 4 is a perspective view of a strength testing apparatus on a cart according to one embodiment of the invention.
Figure 3:
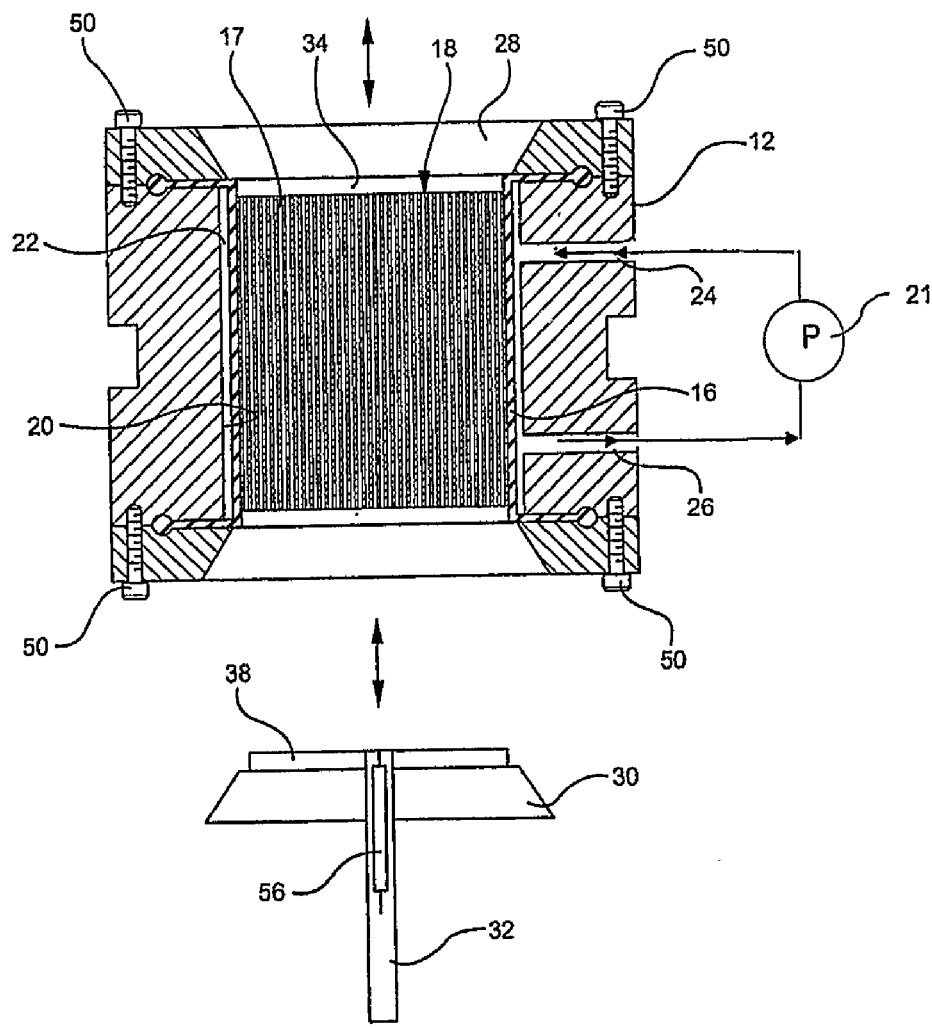

Referring to FIG. 4, preferably, the entire apparatus 10 is sized to fit on a portable cart 60 to facilitate use of the compressive strength testing apparatus 10 in various locations of manufacturing plant. Other optional features of the strength testing apparatus include an operator control panel 62, and an enclosure 64 for housing electrical, pneumatic and hydraulic controls (not shown). The main housing 12, the top plug 28 and the bottom plug 30 and their associated actuators are preferably housed in an enclosure 66. The main housing 12 can be secured to a mounting bracket 68 associated with the cart 60. The top plug 28 and actuator can be mounted on a movable stage 70 capable of moving in the direction of arrow 71. Movable stage can be moved with a pneumatic or hydraulic control system. The inlet 24 and outlet 26 are in fluid communication with a pressure generator, preferably a pressure generator able to produce hydraulic pressure. Preferably, the inlet 24 and outlet 26 are connected to the pressure generator by high pressure hoses and quick connect/disconnect fittings (not shown).

According to certain embodiments, a sensor (not shown) is included and is connected to the testing area and the hydraulic and pneumatic controls for determining failure of the sample during testing. It will be understood that complete or catastrophic failure of the part can be determined by visual inspection of the sample or by detection of an audible crack. However, in certain instances, the part may not catastrophically fail, and a sensor can be included to detect failure of the part. Such sensors may include a pressure sensor connected to the hydraulics of the apparatus to monitor sudden and rapid changes in pressure indicative of a part failure. Upon detection of a sudden pressure change, the apparatus 10 can be equipped with an alarm to alert the operator, or the apparatus can be configured to shut off upon activation of an alarm. Another type of sensor that can be operably connected to the test area of the apparatus is an acoustic sensor capable of detecting cracking in the sample that is not audibly detectable by a human. The acoustic sensor can be connect to an audible and/or visual alarm to alert an operator, or the machine can be configured to shut down upon detection of a crack in a sample.

In use, the apparatus 10 is located in a convenient location for testing honeycomb samples in a manufacturing facility. The stage 70 supporting the top plug 28 and actuator is moved away from the main housing 12 so that sample testing area 18 can be loaded with a sample. The bottom plug 30 is moved upwardly into a closed position by engaging the bottom plug actuator 54, and then the bottom pad 38 is raised to the top of the sample loading area 18 by engaging the bottom pad actuator 57. A sample 17 is loaded on the bottom pad 38, and the bottom pad actuator is engaged to lower the sample 17 into the sample testing area 18. The stage 70 supporting the top plug 28 is moved so that the top plug is located above the sample testing area 18. The top plug actuator is engaged to close the top plug over the sample testing area 18. The pressure generator then supplies fluid pressure through the inlet 24 to the desired testing pressure for the sample 17. Fluid fills the fluid holding area 22, and pressure from the fluid causes the flexible member 16 to exert a compressive force on the periphery of the sample 17. After the sample has been tested to the desired pressure, a signal is sent to the pressure generator, and the fluid exits the fluid holding area 22 through outlet 26. The top plug 28 is then moved upwardly away from the sample testing area, and the stage 70 supporting the top plug is moved away from the sample testing area 18 so that the sample 17 can be unloaded. The bottom pad actuator 56 engages to raise the sample out of the sample testing area 18 so that an operator can remove the sample and load another sample. It will be understood that most of the steps described above, with the exception of the operator loading and unloading the sample on and off the bottom pad are preferably automated and controlled by a control system. In preferred embodiments, the apparatus 10 is adapted to load, test, and unload a sample in less than about 30 seconds, and more preferably, in less than about 15 seconds. Samples can be loaded and unloaded by an operator quickly and easily, without having to reach into the sample testing area.

It will be apparent to those skilled in the art that various modifications and variations can be made to the present invention without departing from the spirit or scope of the invention. Thus, it is intended that the present invention covers modifications and variations of this invention provided they come within the scope of the appended claims and their equivalents.

What is claimed is:

1. An apparatus for testing the compressive strength of a ceramic honeycomb samples comprising:
   a main housing including a generally cylindrical chamber and a generally cylindrical, flexible member disposed within the main housing, the flexible member defining a sample loading and testing area and a gap between the flexible member and the main housing, the gap providing a fluid holding area;

a top plug and a bottom plug for sealing the chamber;

a hydraulic pressure generator for supplying fluid under pressure to the fluid holding area and to expand the flexible member to provide uniform pressure on the periphery of the sample; and means for automatically moving samples in and out the sample loading and testing area, wherein the means for automatically moving samples in at out the sample loading and testing area includes a retractable plunger.

2. The apparatus of claim 1, wherein the apparatus is adapted to load, test, and unload a sample in less than about 30 seconds.

3. The apparatus of claim 1, wherein the flexible member comprises a generally cylindrical main body, top and bottom flanges integrally formed with the main body, extending radially from the top and bottom of the main cylinder and including integral gaskets for sealing with the main body.

4. The apparatus of claim 1, wherein the apparatus is adapted to load, test, and unload a sample in less than about 15 seconds.

5. The apparatus of claim 4, wherein the top plug, bottom plug and the plunger are retractable and pneumatically controlled.

6. The apparatus of claim 5, wherein the apparatus is sized to fit on a portable cart.

7. The apparatus of claim 6, further including a sensor for determining failure of the sample.

8. The apparatus of claim 7, wherein the sensor is a pressure sensor.

9. The apparatus of claim 7, wherein the sensor is an acoustic sensor.

* * * * *

UNITED STATES PATENT AND TRADEMARK OFFICE
CERTIFICATE OF CORRECTION

| | | |
|---|---|---|
| PATENT NO. | : 6,729,190 B1 | Page 1 of 2 |
| APPLICATION NO. | : 10/282638 | |
| DATED | : May 4, 2004 | |
| INVENTOR(S) | : Boyko et al. | |

Figure 3:
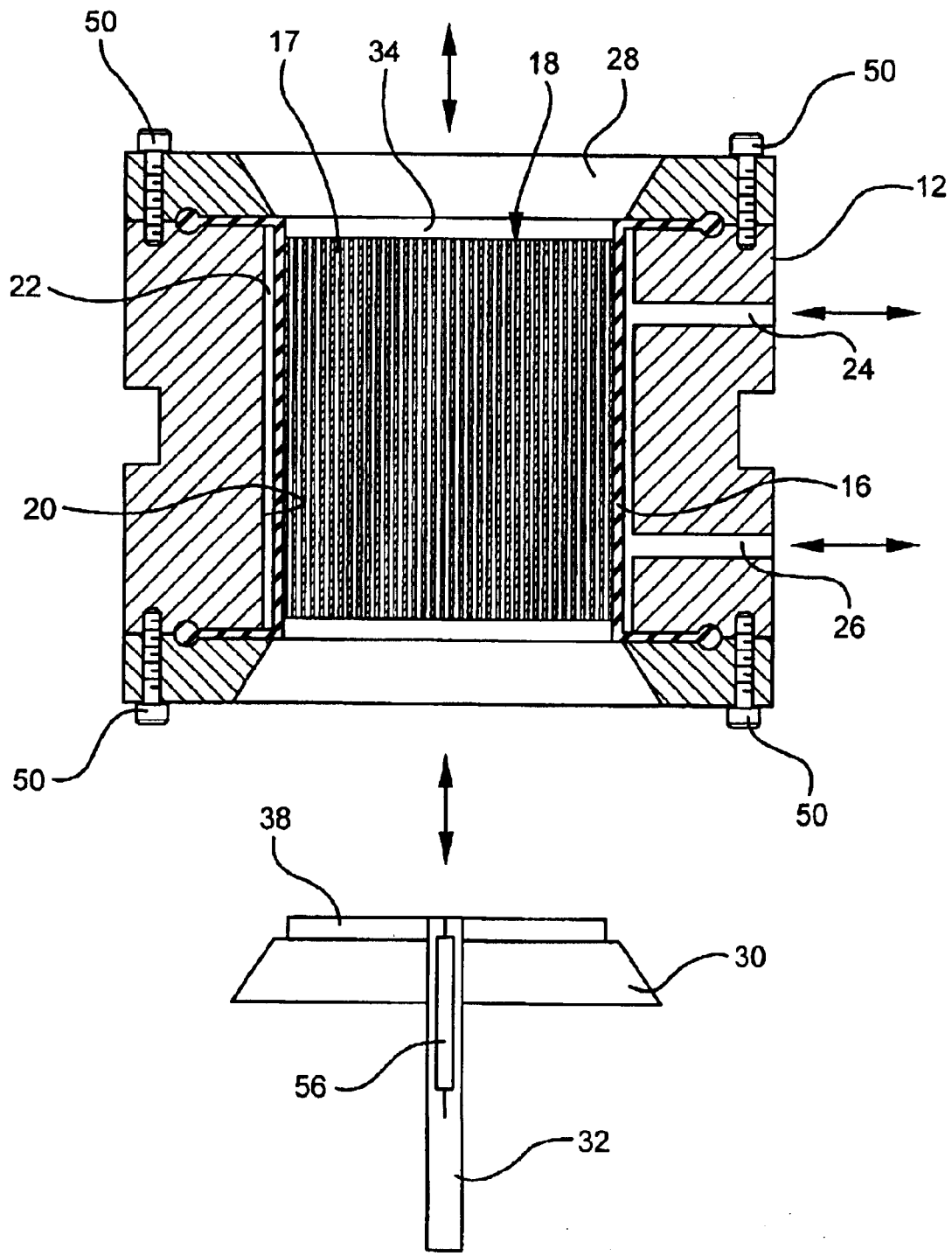
FIG. 3 is an assembled cross-sectional view of a main housing used in a strength testing apparatus according to one embodiment of the invention.

It is certified that error appears in the above-identified patent and that said Letters Patent is hereby corrected as shown below:

Sheet 3 of 4, Fig. 3, the hydraulic pressure generator with reference numeral 21, is missing. See attached Signed and Sealed this Twenty-eighth Day of August, 2007

JON W. DUDAS
*Director of the United States Patent and Trademark Office*